(12) United States Patent
Rosen et al.

(10) Patent No.: US 9,220,851 B2
(45) Date of Patent: Dec. 29, 2015

(54) OPEN AND CLOSED VALVE MEDICATION DELIVERY SYSTEM FOR HIGH PRESSURE INJECTIONS

(75) Inventors: Melissa Rosen, Lynn, MA (US); Michel Bruehwiler, Newton, MA (US); Ryan Schoonmaker, Salem, MA (US); Ira Spool, Brookline, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1209 days.

(21) Appl. No.: 12/998,852

(22) PCT Filed: Dec. 8, 2009

(86) PCT No.: PCT/US2009/006423
§ 371 (c)(1),
(2), (4) Date: Sep. 20, 2011

(87) PCT Pub. No.: WO2010/077280
PCT Pub. Date: Jul. 8, 2010

(65) Prior Publication Data
US 2012/0004640 A1    Jan. 5, 2012

Related U.S. Application Data

(60) Provisional application No. 61/193,595, filed on Dec. 9, 2008.

(51) Int. Cl.
*A61M 5/48* (2006.01)
*A61M 5/20* (2006.01)
(Continued)

(52) U.S. Cl.
CPC ............... *A61M 5/48* (2013.01); *A61M 5/204*
(2013.01); *A61M 5/31541* (2013.01); *A61M 5/31551* (2013.01); *A61M 5/31568* (2013.01); *A61M 2005/3103* (2013.01)

(58) Field of Classification Search
CPC ..... A61M 5/19; A61M 5/204; A61M 5/3155; A61M 5/31551; A61M 5/31553
USPC ......................................... 604/191, 211, 247
See application file for complete search history.

(56) References Cited

U.S. PATENT DOCUMENTS

| 4,643,723 A | 2/1987 | Smit |
| 4,755,169 A * | 7/1988 | Sarnoff et al. ................ 604/511 |

(Continued)

FOREIGN PATENT DOCUMENTS

| JP | 62502876 | 8/1987 |
| JP | H06505415 | 6/1994 |

(Continued)

OTHER PUBLICATIONS

JP Office Action issued in JP Patent Application No. 2011-540690 dated Sep. 24, 2013.
(Continued)

*Primary Examiner* — Kami A Bosworth
(74) *Attorney, Agent, or Firm* — Dickinson Wright PLLC

(57) ABSTRACT

A dual-chambered drug delivery device (301) includes a first chamber (342) in which medicament is stored and a second chamber (331) in fluid communication with the first chamber (342). A medicament dose is transferred to the second chamber (331) from the first chamber (342) prior to injecting the medicament dose. A needle (363) communicates with the second chamber (331) for injecting the medicament dose into an injection site.

19 Claims, 18 Drawing Sheets

(51) Int. Cl.
  *A61M 5/315* (2006.01)
  *A61M 5/31* (2006.01)

(56) References Cited

U.S. PATENT DOCUMENTS

| | | | |
|---|---|---|---|
| 5,147,323 A | 9/1992 | Haber | |
| 5,279,585 A | 1/1994 | Balkwill | |
| 5,279,586 A | 1/1994 | Balkwill | |
| 5,298,023 A | 3/1994 | Haber | |
| 5,433,191 A * | 7/1995 | Haber et al. | 128/200.14 |
| 5,456,672 A | 10/1995 | Diederich | |
| 5,549,575 A | 8/1996 | Giambattista | |
| 5,569,214 A | 10/1996 | Chanoch | |
| 5,582,598 A | 12/1996 | Chanoch | |
| 5,674,204 A | 10/1997 | Chanoch | |
| 5,843,042 A | 12/1998 | Ren | |
| 5,921,966 A | 7/1999 | Bendek | |
| 5,944,700 A | 8/1999 | Nguyen | |
| 5,957,896 A | 9/1999 | Bendek | |
| 6,042,571 A | 3/2000 | Hjertman | |
| 6,056,728 A | 5/2000 | von Schuckmann | |
| 6,096,010 A | 8/2000 | Walters | |
| 6,221,053 B1 | 4/2001 | Walters | |
| 6,248,095 B1 | 6/2001 | Giambattista | |
| 6,277,099 B1 | 8/2001 | Strowe | |
| 6,364,865 B1 * | 4/2002 | Lavi et al. | 604/411 |
| 6,537,242 B1 | 3/2003 | Palmer | |
| 6,652,483 B2 | 11/2003 | Slate | |
| 6,689,101 B2 | 2/2004 | Hjertman | |
| 6,932,794 B2 | 8/2005 | Giambattista | |
| 6,936,032 B1 | 8/2005 | Bush, Jr. | |
| 6,986,758 B2 | 1/2006 | Schiffmann | |
| 7,018,364 B2 | 3/2006 | Giambattista | |
| 7,169,132 B2 | 1/2007 | Bendek | |
| 7,217,253 B2 | 5/2007 | Slate | |
| 2001/0037087 A1 * | 11/2001 | Knauer | 604/137 |
| 2003/0040715 A1 | 2/2003 | D'Antonio | |
| 2005/0165363 A1 | 7/2005 | Judson | |
| 2007/0060894 A1 * | 3/2007 | Dai et al. | 604/207 |
| 2009/0043264 A1 * | 2/2009 | Glejbol et al. | 604/211 |

FOREIGN PATENT DOCUMENTS

| | | |
|---|---|---|
| JP | 2004508897 | 3/2002 |
| JP | 2003126252 | 5/2003 |
| JP | 2008538719 | 11/2008 |
| WO | 02/24259 A2 | 3/2002 |
| WO | 2004108193 A1 | 12/2004 |
| WO | WO 2007/113318 | 10/2007 |

OTHER PUBLICATIONS

English Translation of Official Notice of Rejection Mailed Jun. 3, 2014, Issued in JP Patent Application No. 2011-540690, 2 pages.

* cited by examiner

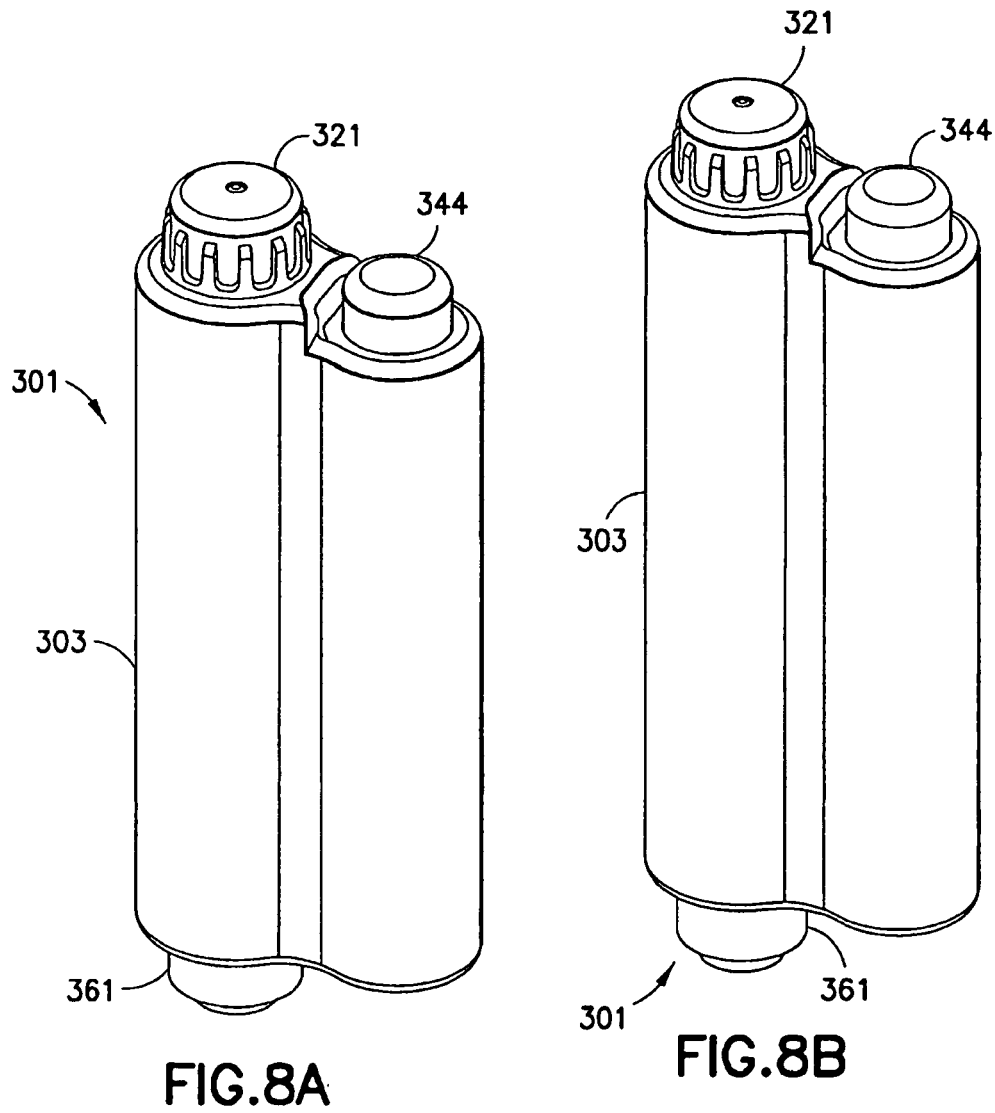

OPEN AND CLOSED VALVE MEDICATION DELIVERY SYSTEM FOR HIGH PRESSURE INJECTIONS

CROSS REFERENCE TO RELATED APPLICATION

This application claims the benefit under 35 U.S.C. §119 (e) of U.S. Provisional Application Ser. No. 61/193,595, filed Dec. 9, 2008, the entire content of which is hereby incorporated by reference.

FIELD OF THE INVENTION

The present invention relates generally to a drug delivery device that facilitates high pressure medication injections. More particularly, the present invention relates to a drug delivery device that diverts high pressures away from the original drug container to prevent medication leakage and inaccurate doses. Still more particularly, the present invention relates to a drug delivery device having a secondary chamber that amplifies the injection force, thereby facilitating intradermal medication injections.

BACKGROUND OF THE INVENTION

Insulin and other injectable medications are commonly given with syringes into the intradermal layer of the skin and other dense tissues. Intradermal medication injections result in faster uptake of the medication, thereby resulting in improved therapy. Such injections require higher injection pressures, upwards of 200 psi, than traditional subcutaneous injections.

Techniques and devices are known for administering an injection into the intradermal region of the skin. One method, commonly referred to as the Mantoux technique, uses a "standard" needle and syringe, i.e., a syringe typically used to administer intramuscular or subcutaneous injections. The health care provider administering the injection follows a specific procedure that requires a somewhat precise orientation of the syringe with regard to the patient's skin as the injection is administered. The health care provider must also attempt to precisely control the penetration depth of the needle into the patient's skin to ensure that it does not penetrate beyond the intradermal region. Such a technique is complicated, difficult to administer, and often may only be administered by an experienced health care professional.

As advances in understanding the delivery of drug proceeds, the use of intradermal delivery systems is expected to increase. However, use of a "standard" length needle to deliver a drug substance intradermally has its shortcomings, as noted above. Moreover, it is not possible to use a delivery device having a needle length suited for intradermal injection to aspirate a syringe with drug substance from a multi-use vial. Thus, there are shortcomings in the prior art that prevent administering an intradermal injection using a "standard" length needle and a multi-use vial. It would be advantageous to have a drug delivery device capable of accessing substances stored in multi-dose vials and delivering such substances into the intradermal region of the skin without encountering the shortcomings described above.

A conventional syringe 101 is shown in FIG. 1. The needle 103 is sufficiently long to deliver the drug to the subcutaneous region of the skin. However, a user would not be able to easily deliver the drug to the intradermal region of the skin, as discussed above.

Existing drug delivery pens offer several advantages over syringe-based systems for delivering insulin subcutaneously. Reusable drug delivery pens hold 20 or more doses without requiring the drug cartridge to be refilled. Dose setting is achieved simply with the use of a dial. However, those injection systems are designed for low pressure subcutaneous injections. Intradermal injection of insulin and other medications provides faster uptake of the drug, thereby leading to improved therapy. Existing drug delivery pens have several limitations regarding intradermal drug delivery. First, the mechanical advantage provided by the pen is minimal and requires the user to supply upwards of 20 lbs of force to generate sufficient pressure. Secondly, the pen components can be damaged by this high force, resulting in leaking and inaccuracy at the high pressures.

Drug delivery pens, such as the exemplary drug delivery pen 100 shown in FIGS. 2 and 3, are designed for subcutaneous injections and typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location and provide cover/protection from accidental needle injury.

FIG. 3 is an exploded view of the drug delivery pen 100 of FIG. 2. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

The backpressure in subcutaneous injections is not very large, while the backpressure associated with intradermal injections may be many times greater than that of subcutaneous injections. For example, the backpressure often exceeds 200 psi for an intradermal injection, while the backpressure for a subcutaneous injection is generally in the range of 30-50 psi. Accordingly, in view of the large force required to inject medication into the intradermal layer with existing drug delivery pens, injecting the medication intradermally is difficult. A need exists for a drug delivery pen that has a high mechanical advantage to reduce thumb forces required to overcome the initial high breakout force in the cartridge during an intradermal injection.

Furthermore, the drug delivery pen components can be damaged due to being subjected to the high pressures associated with intradermal injections, thereby resulting in medication leakage and dose inaccuracy. Accordingly, a need exists for a drug delivery device that diverts the large pressures associated with an intradermal injection from the original medication container.

SUMMARY OF THE INVENTION

In accordance with an aspect of the present invention, a drug delivery device is provided that facilitates injecting insulin or other medications at high pressures.

In accordance with another aspect of the present invention, a drug delivery device has a secondary chamber that amplifies the injection force, thereby facilitating intradermal medication injections.

In accordance with yet another aspect of the present invention, high pressures associated with intradermal injections are diverted from the original medication container to prevent medication leakage and inaccurate doses.

In accordance with another aspect of the present invention, a drug delivery device is compact, thereby increasing usability and portability of the device.

The drug delivery device operates in a similar manner to existing reusable drug delivery pens. A disposable needle is attached to the drug delivery device, the user dials a dose, inserts the needle into the skin at an injection site, and then injects the medication. The drug delivery device has a system that transports a user-determined bolus of the medication from an original medication container (or cartridge) to a secondary chamber using a compression spring to provide a force on the container. The secondary chamber employs a smaller cross sectional area than the original medication container to amplify injection pressure at a given input force. The user sets the desired dose via a dose setting knob similar to existing drug delivery pens. When the dose is set, the dose is moved to the secondary chamber using a spring that supplies a force on the drug container. After the needle is inserted, the plunger is depressed to inject the dose into the patient.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which:

FIGS. 8A-8D are perspective views of a drug delivery device according to another exemplary embodiment of the present invention;

Throughout the drawings, like reference numbers will be understood to refer to like parts, components and structures.

DETAILED DESCRIPTION OF THE EXEMPLARY EMBODIMENTS

Figure 1:
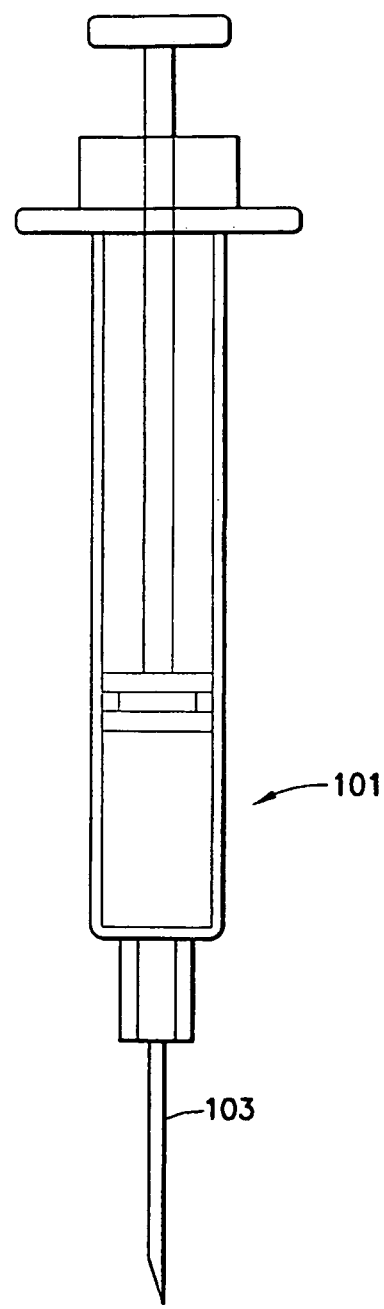
FIG. 1 is a front elevational view of a syringe.

The drug delivery device according to exemplary embodiments of the present invention allows the user to inject medication at high pressures with lower input forces by decoupling the primary (original) drug container and its cross sectional area from the injection mechanics.

The drug delivery device has advantages in improved dose accuracy and reduced medicament leakage over existing drug delivery pens 100 (FIGS. 2 and 3) by diverting high pressures away from the original medicament container (cartridge 12). At high pressures, the drug container stopper 15 can deform, which changes the volume and results in dose inaccuracies. Additionally, when the stopper 15 is allowed to equilibrate and return to its natural volume after the needle 11 is removed from the intradermal space and the back pressure dissipates, unwanted expulsion of the drug can occur.

In an exemplary embodiment of the present invention shown in FIGS. 4-7, a dual-chambered drug delivery device 201 injects insulin, high viscosity medicaments, or other medicaments at high pressures. A disposable needle 203 is attached to the end of the device 201, which houses an original medicament container (cartridge) or first chamber 211. Preferably, the needle 203 is an intradermal needle. Alternatively, the needle may be a subcutaneous needle. Preferably, the needle is a small gauge needle, such as a 34 gauge needle.

The user dials a dose on the dose set knob 213, inserts the needle 203, and then injects the medicament. The drug delivery device 201 diverts the high pressure from the original drug container, first chamber, 211 to prevent medicament leakage and inaccurate doses.

The injection pressure is decoupled from the original medicament container 211 by moving the medicament dose to a secondary chamber 221 via a conduit (fluid channel) 231 using a pressure (created by the user input force that releases compression spring 243) in the first chamber 211 and a two-valve system for injecting the dialed dose from the secondary chamber 221 into the patient. The first and second chambers are disposed in a housing 225. A lever 245 extending outwardly from the housing 225 is operated by the user to release the compression spring 243. The first valve 233 opens to allow the secondary chamber 221 to fill while the second valve 235 is closed. During injection, the first valve 233 closes and the second valve 235 opens to allow the medicament dose to be injected. The secondary chamber 221 has a smaller cross sectional area than the first chamber 211, thus providing higher pressure with the same user input force.

Figure 7:
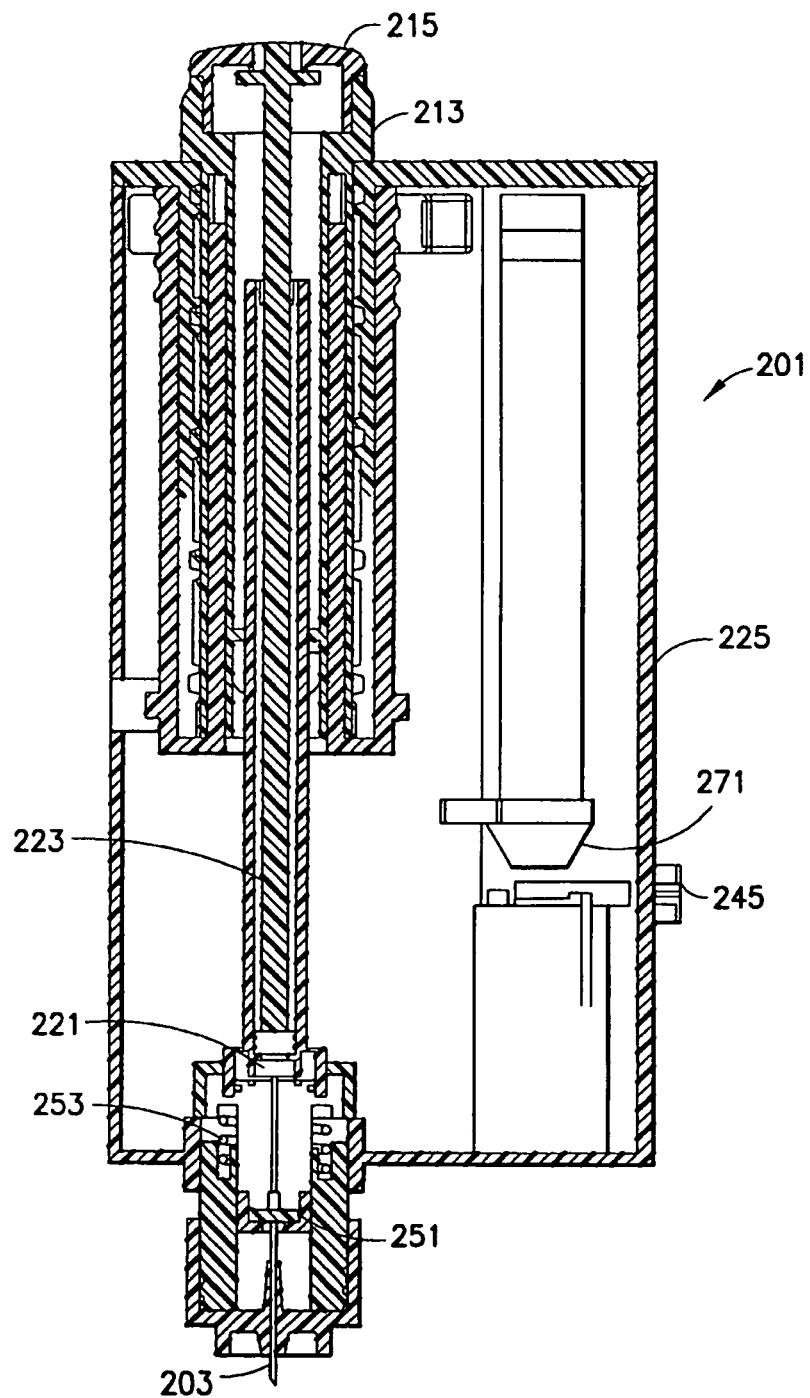
FIG. 7 is an elevational view in cross section of the drug delivery device of FIG. 4.
Figure 8C:
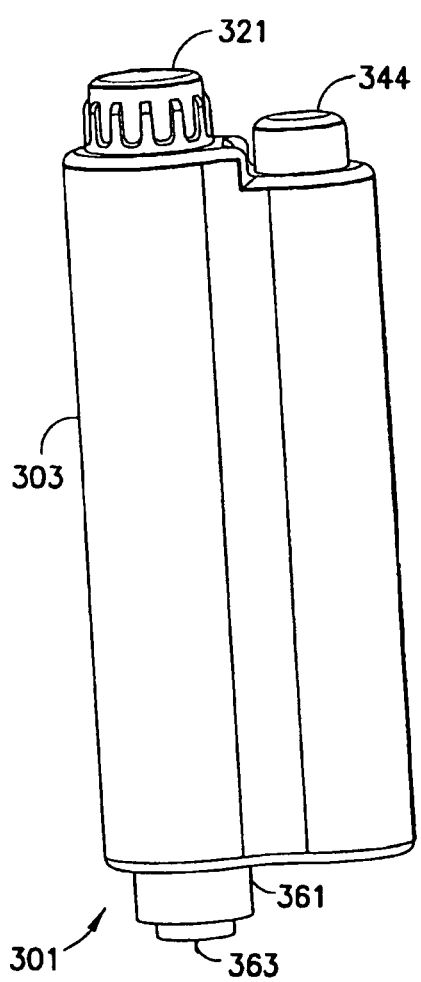
Figure 8D:
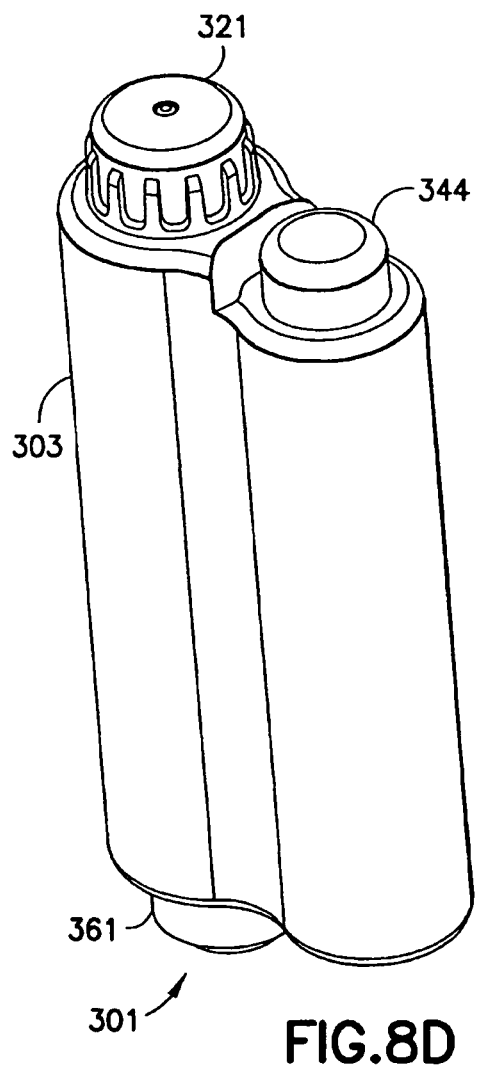

Using the relationship of pressure, force and area, P=F/A, a chamber with half the cross sectional area produces twice the pressure at a given load. A first longitudinal axis through the needle 203 is parallel to and spaced from a second longitudinal axis through the cartridge 211, as shown in FIG. 7.

Dose accuracy and drooling issues related to cartridge stopper effects under high pressure in existing drug delivery pens 100 (FIGS. 2 and 3) are reduced by decoupling the high injection pressure from the primary medicament container (first chamber 211) and into a less-pressure sensitive (in terms of deformation) secondary chamber 221 and stopper.

Further, dose accuracy is higher than that of existing drug delivery pens as the stopper travel distance to deliver 1 unit of medicament out of the smaller secondary chamber 221 is approximately 1 mm when compared to the approximately 0.15 mm stopper travel distance to deliver 1 unit out of the larger primary drug container (first chamber 211). This improved dose accuracy over existing drug delivery pens 100 (FIGS. 2 and 3) is significant, particularly at low dose ranges.

Figure 2:
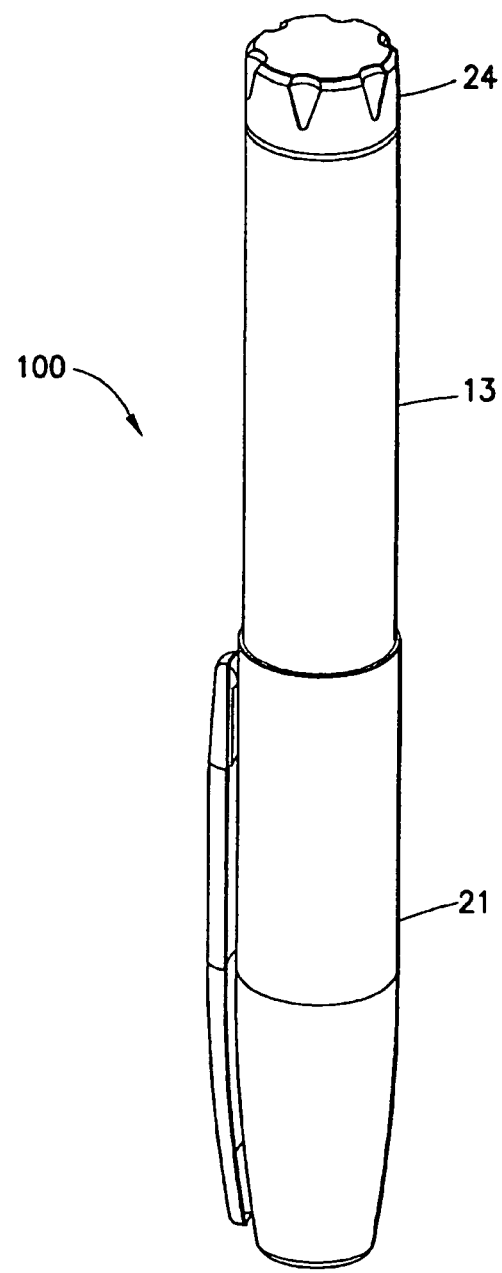
FIG. 2 is a perspective view of a drug delivery pen.
Figure 3:
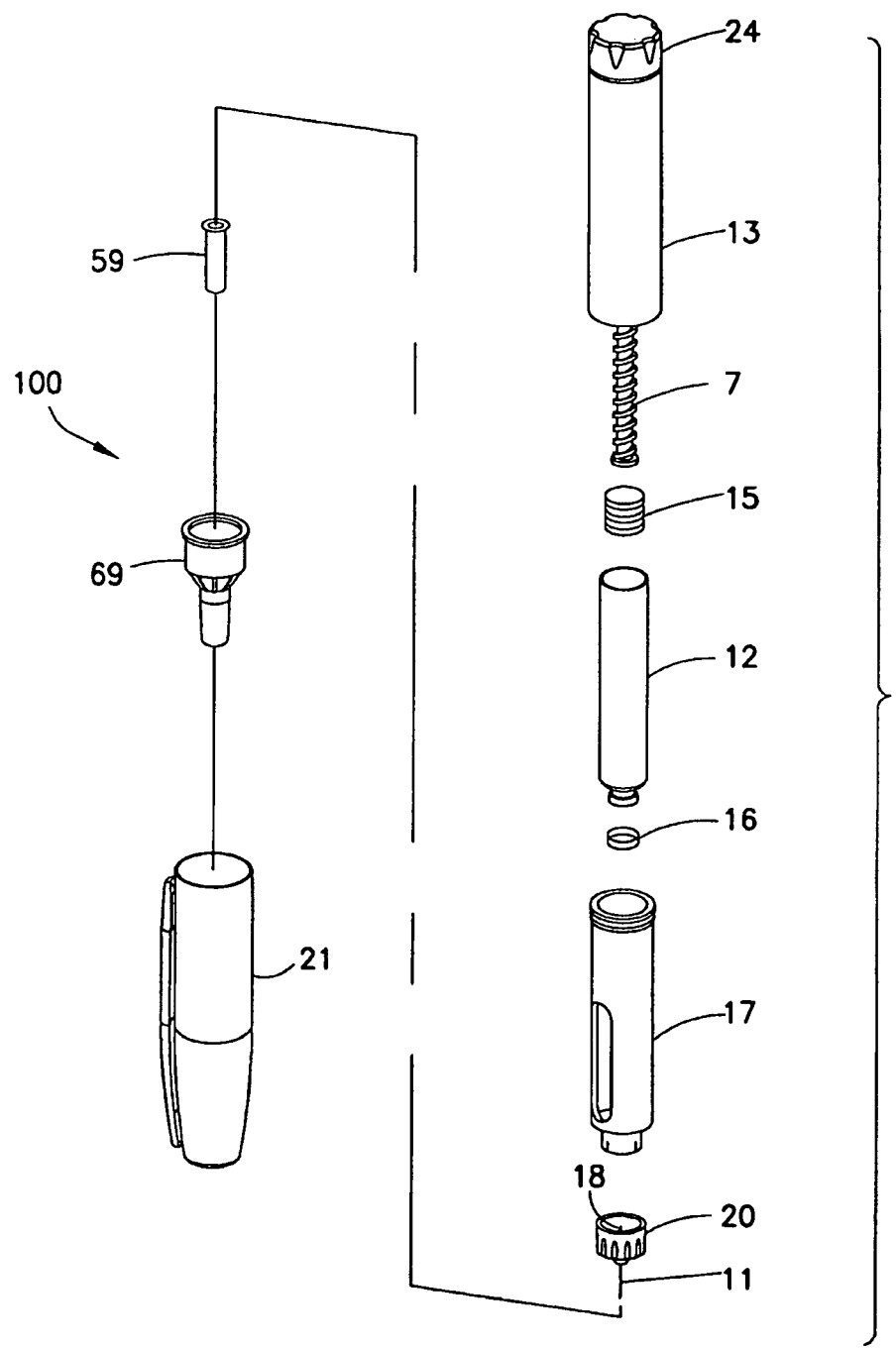
FIG. 3 is an exploded perspective view of the drug delivery pen of FIG. 2.
Figures 4B, 4C:
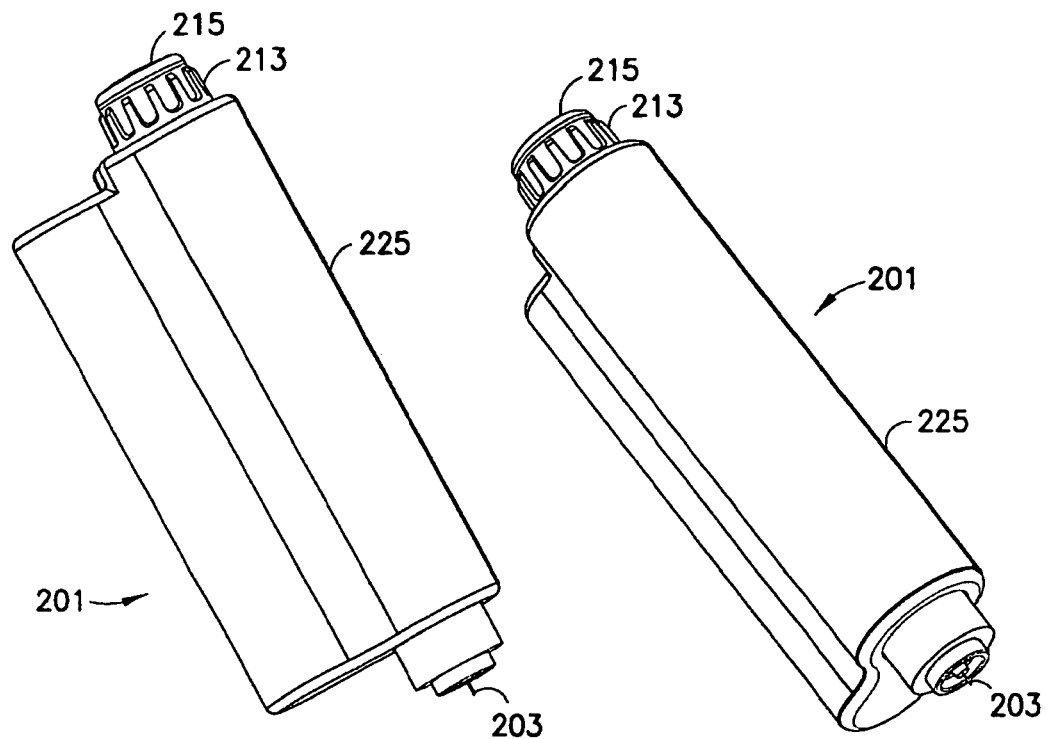
FIGS. 4A-4C is a perspective view of a drug delivery device according to an exemplary embodiment of the present invention.
Figure 4A:
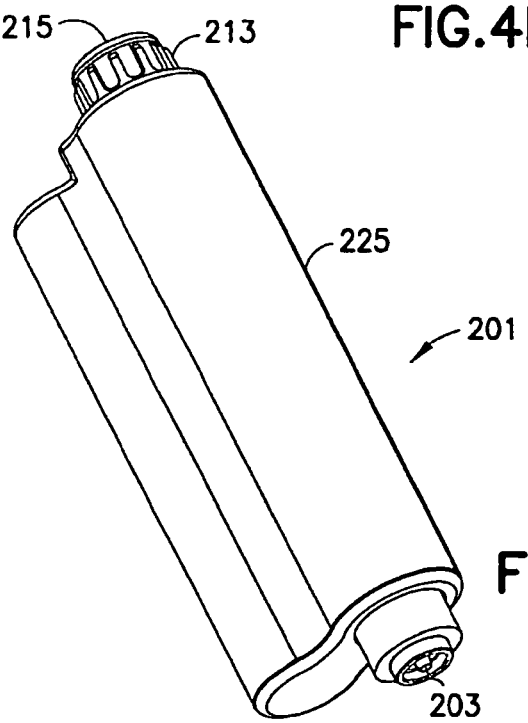
Figure 5:
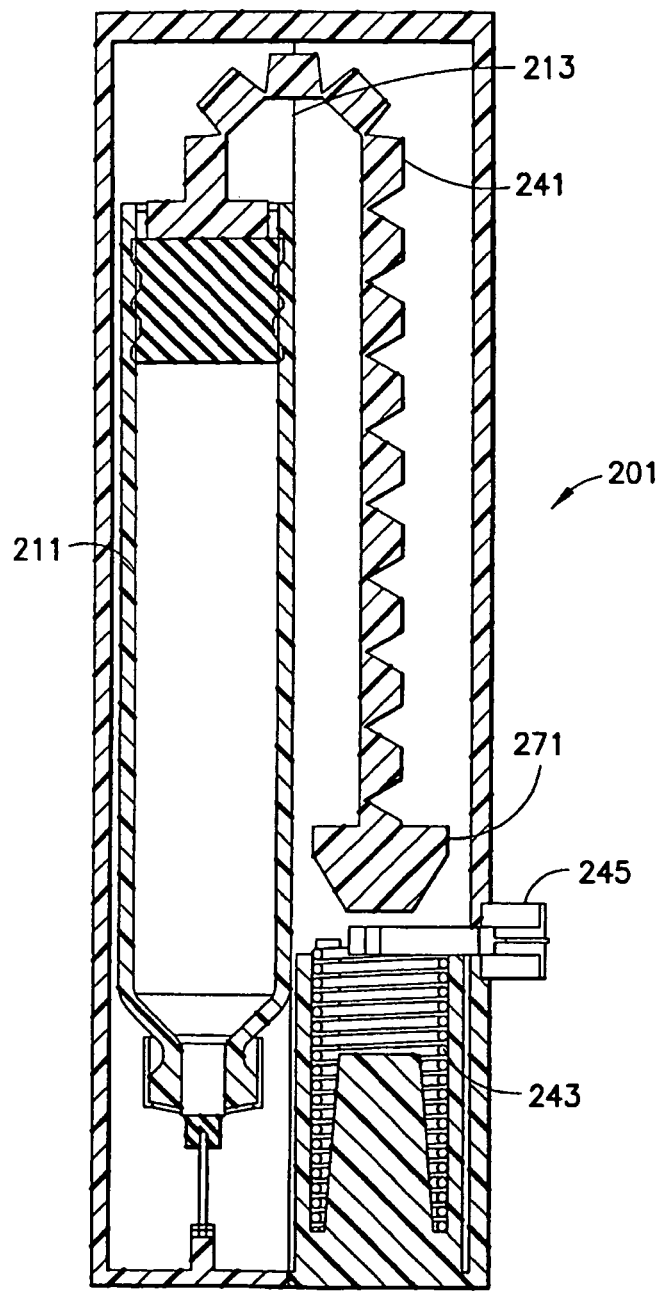
FIG. 5 is an elevational view in cross section of the drug delivery device of FIGS. 4A-4C.
Figure 6A:
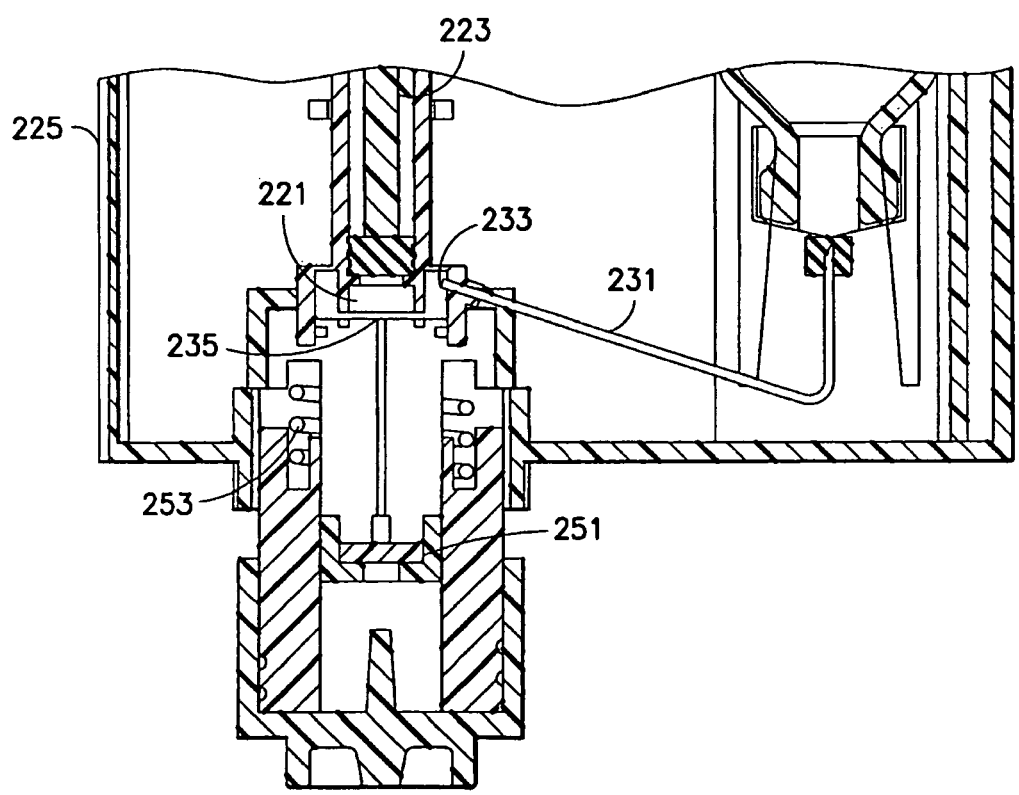
FIGS. 6A and 6B are elevational views in cross section of a conduit connecting the original medication container and the secondary chamber.
Figure 6B:
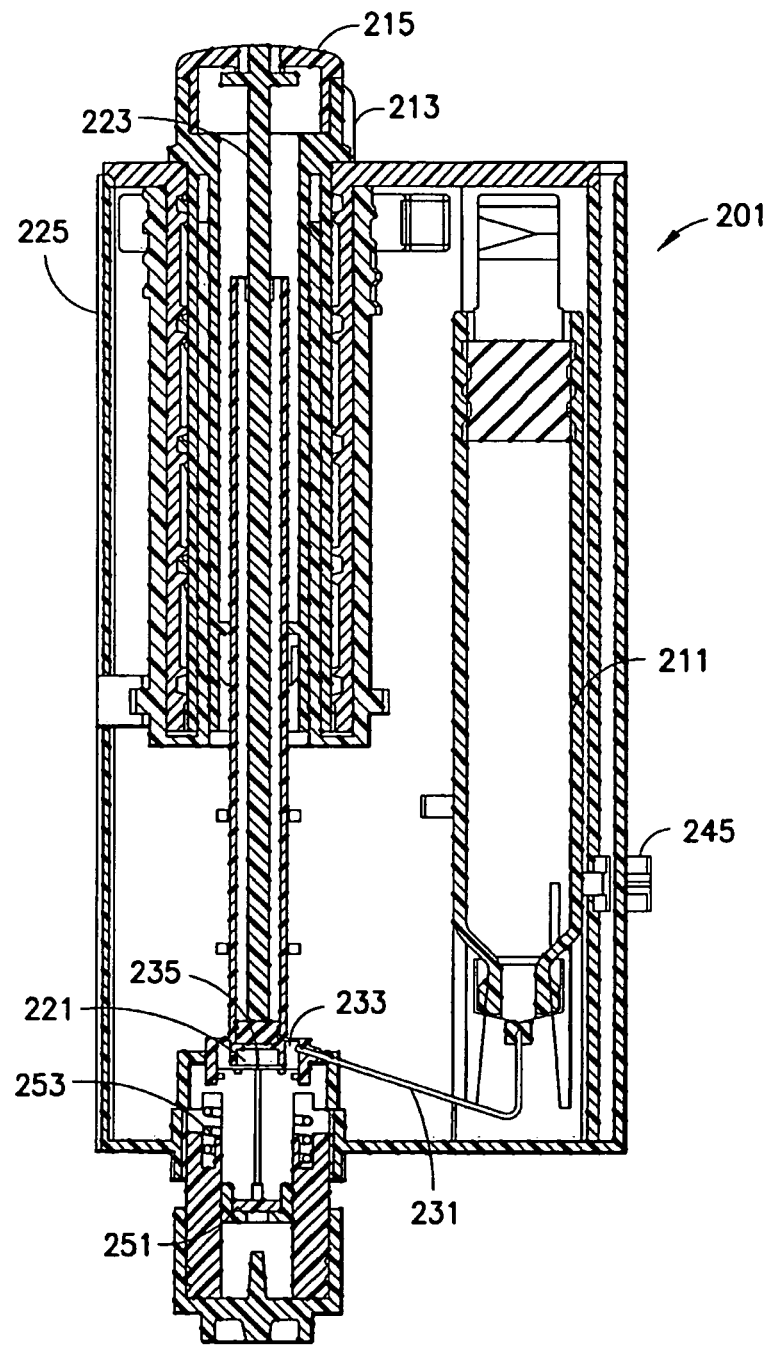

Component deformation due to high pressure (or user force) is also limited as the user force is applied via a rotating thumb button 215 directly to the linearly plunger rod 223 of the smaller second chamber 221, eliminating the need for complicated force transfer and amplification mechanisms (user to stopper 15) often used in existing drug delivery pens 100 (FIGS. 2 and 3). In most existing drug delivery pens 100, the dose delivered is the result of a linear displacement of a drive screw 7 that translates a given length dependent on the dialed bolus volume. The dialed bolus determines the stroke length of the injection. The user imparts a force on the injection button 24 and completes the stroke length of the injection. The force and stroke of the injection motion are translated into a torque. The torque is then used to drive the drive screw 7 linearly forward. This type of system produces inaccuracies at the low end of the dosing range due to the complex relationship between the initial stroke and the final drive screw motion.

Alternatively, because the cross sectional area of the second chamber 221 in the present invention is smaller than that of most existing drug delivery pens 100, the torque used to drive the system is significantly less, while using the same linear method for injection.

After the initial priming mechanism of the primary drug container 211 is engaged, the compression spring 243 is released, pressurizing the primary drug container via a bendable rack 241.

Medicament is moved from the first chamber 211 through the conduit 231 into the second chamber 221 that has the first valve 233 and the second valve 235. The filling of the second chamber 221 is accomplished by exerting a force $F_{cs}$ on the first chamber 211 using a compression spring 243 that creates a pressure greater than the opening pressure of the first valve 233 ($V_1$). The force from the injection causes the thin shoulder of the first valve 233 ($V_1$) to deflect, because this force is less than the friction force of the plunger 223, and closes the first valve 233 ($V_1$). The second valve 235 ($V_2$) is only opened when the reactive force from the skin during injection is great enough to compress the second spring 251 due to sliding components, thereby moving the needle 203 through the septum 253.

The exemplary embodiment of FIGS. 4-7 may also include a dose tracking system that upon spring engagement uses a hinged rack 241 to track the stopper 261 displacement inside the first chamber 211. The dose set knob 213 is coupled rotationally with an externally threaded component 271 that is fixed rotationally, but is allowed to slide within the device. As the medicament is emptied from the first chamber 211, the hinged rack 241 advances until the foot 271 collides with the threaded nut 273, preventing further dose setting with the limited medicament available in the first chamber 211. Alternatively, the medicament dose may also be tracked by a nut integrated into the dose setting mechanism. This nut tracks the cumulative dose delivered and prevents the user from setting a larger dose than the available medicament as the nut engages with a mechanical stop. This allows for a more compact device design.

The second chamber 221 has a smaller cross sectional area than the first chamber thus providing higher pressure using the same input force. Standard 3.0 mL insulin cartridges (first chamber 211) have a diameter of approximately 9.7 mm, thereby resulting in a cross sectional area of $A=\pi r^2=4.85^2*3.14159=73.9$ mm$^2$.

The second chamber 221 of the drug delivery device 201 may have a diameter of 3.5 mm resulting in cross sectional area of $1.75^2*3.14159=9.62$ mm$^2$. For a given pressure, P, a force multiplication is achieved using the following relationships: $P=F_1/A_1$, $P=F_2/A_2$. Therefore, $F_1/A_1=F_2/A_2$. The force multiplier $M_f$, $F_1/F_2$ becomes the ratio of the areas, $A_1/A_2$, $M_f=73.9/9.62=7.7$.

Therefore, an exemplary embodiment of the present invention requires approximately seven (7) times less force to achieve the same injection pressure as a drug delivery device 100 (FIGS. 2 and 3) that applies force directly to the medicament cartridge 12 without force amplification.

Another exemplary embodiment of a dual-chambered drug delivery device 301 of the present invention is shown in FIGS. 8-21. The drug delivery device 301 operates similarly to the exemplary embodiment shown in FIGS. 4-7. A dose is set, the secondary chamber is filled, and the dose is delivered intradermally.

Figure 9:
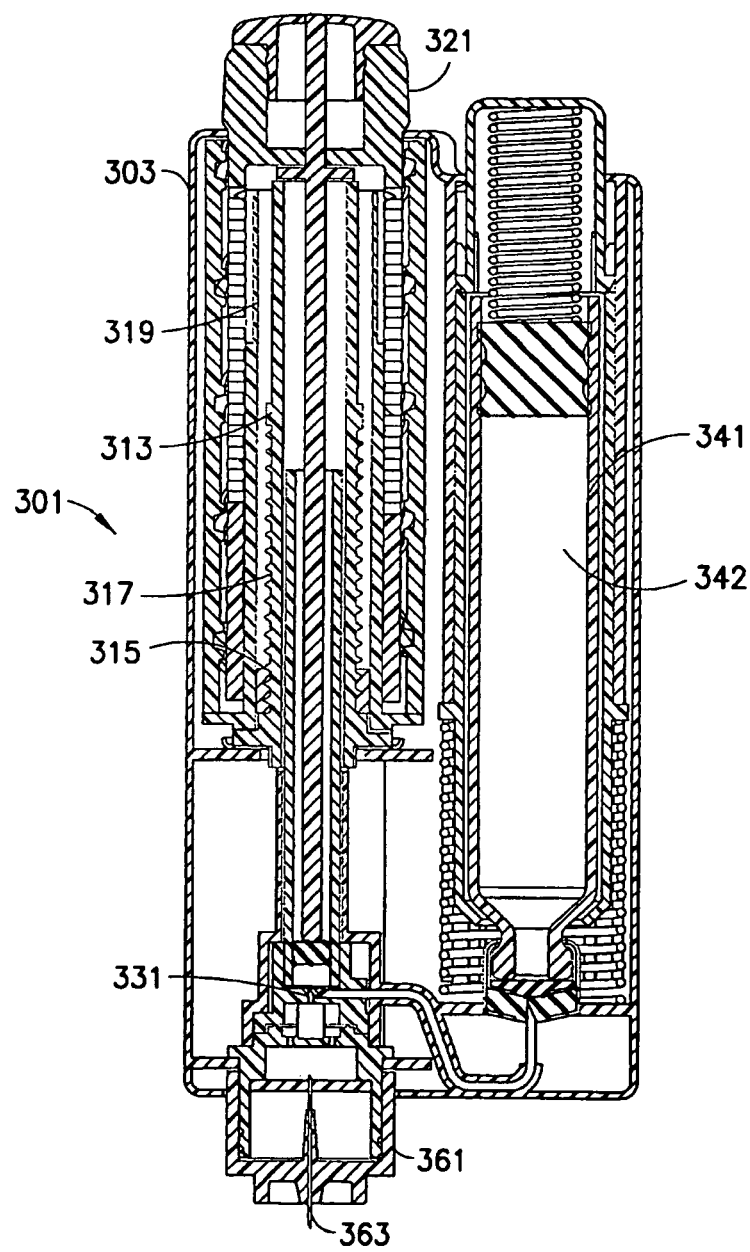
FIG. 9 is an elevational view in cross section of the drug delivery device of FIGS. 8A-8D.
Figure 10:
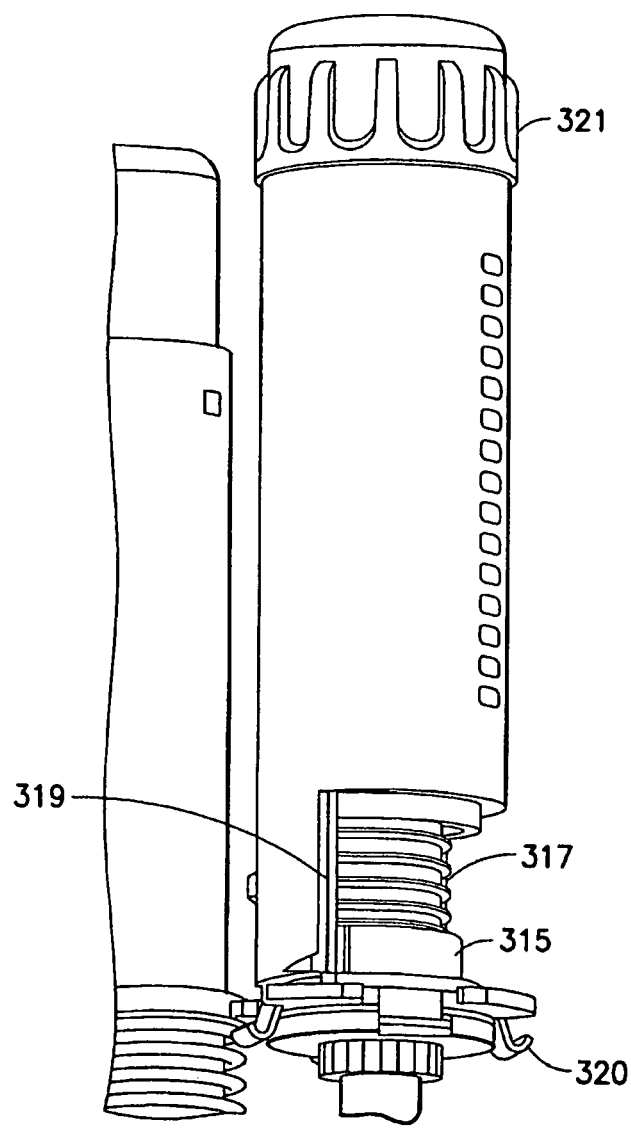
FIGS. 10-15 illustrate setting the dose in the drug delivery device of FIGS. 8A-8D.
Figure 12:
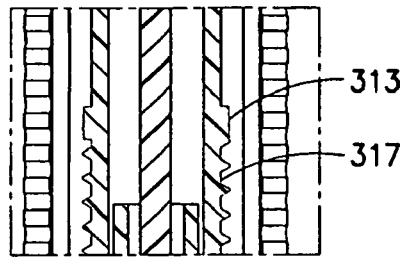
Figure 11:
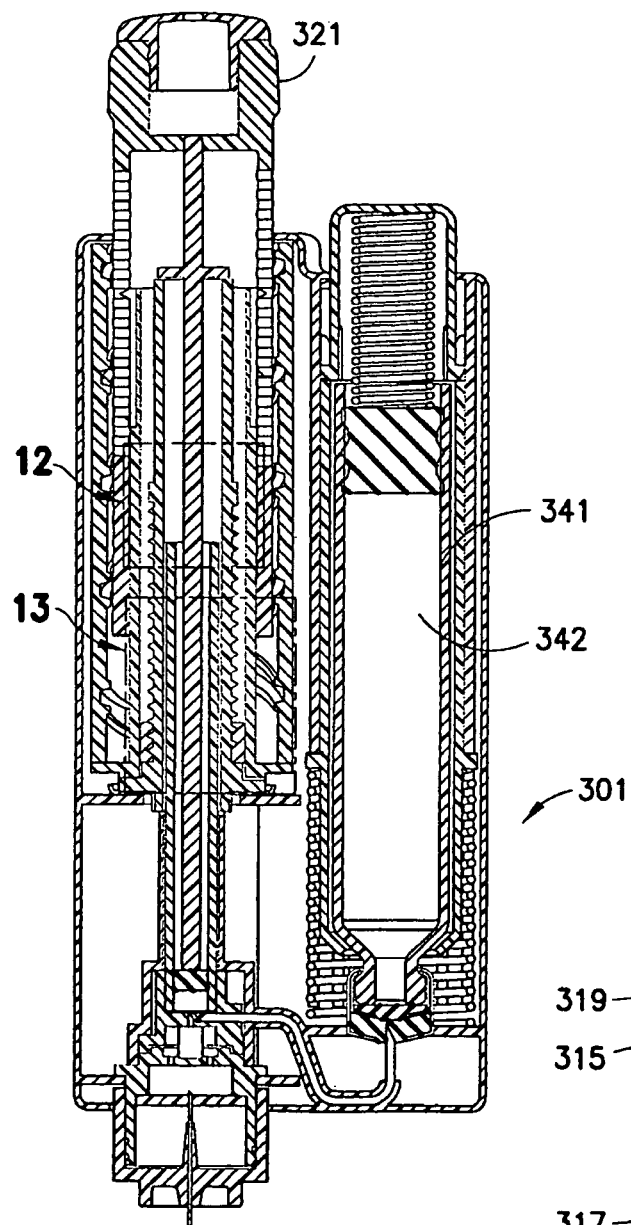
Figure 13:
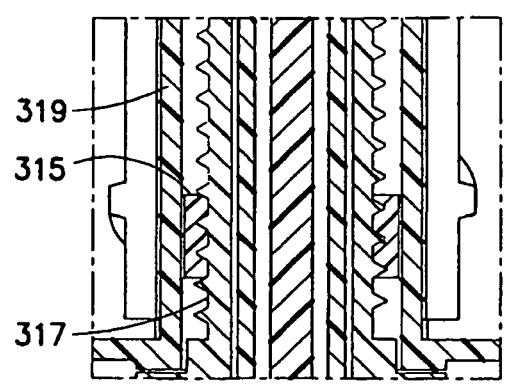

A cartridge 341 is movably disposed in the housing 303. The cartridge 341 has a first chamber 342 in which a medicament is stored. An end 344 of the first chamber 341 extends externally of the housing 303. A second chamber 331 is in fluid communication with the first chamber 342. The first chamber 342 and the second chamber 331 are disposed in a housing 303. A needle hub 361, in which an intradermal needle 363 is rigidly fixed, is threadably engaged with the housing 303. As shown in FIG. 9, a first longitudinal axis through the needle 363 is parallel to and spaced from a second longitudinal axis through the cartridge 341.

Figures 14, 15:
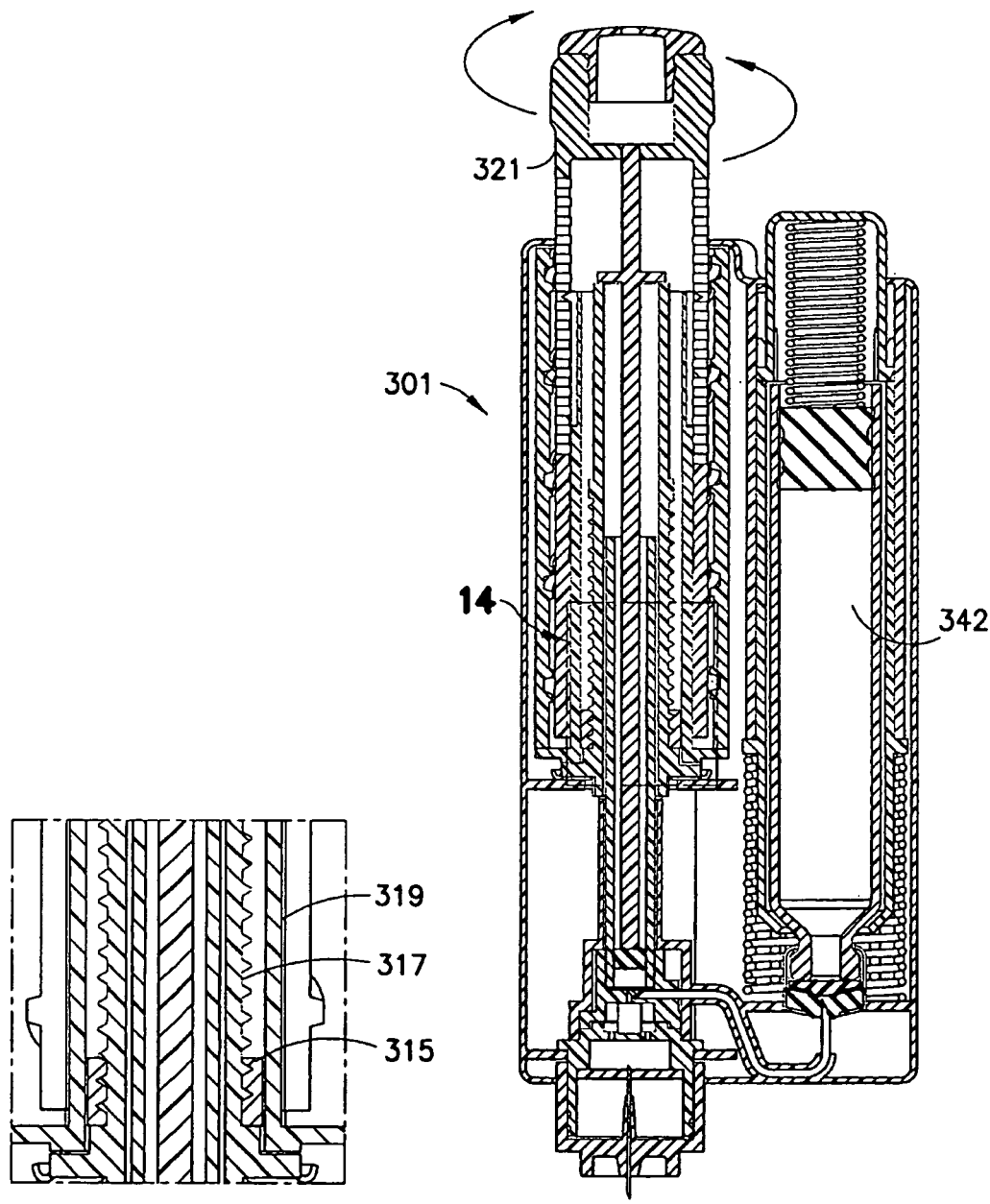
Figure 16:
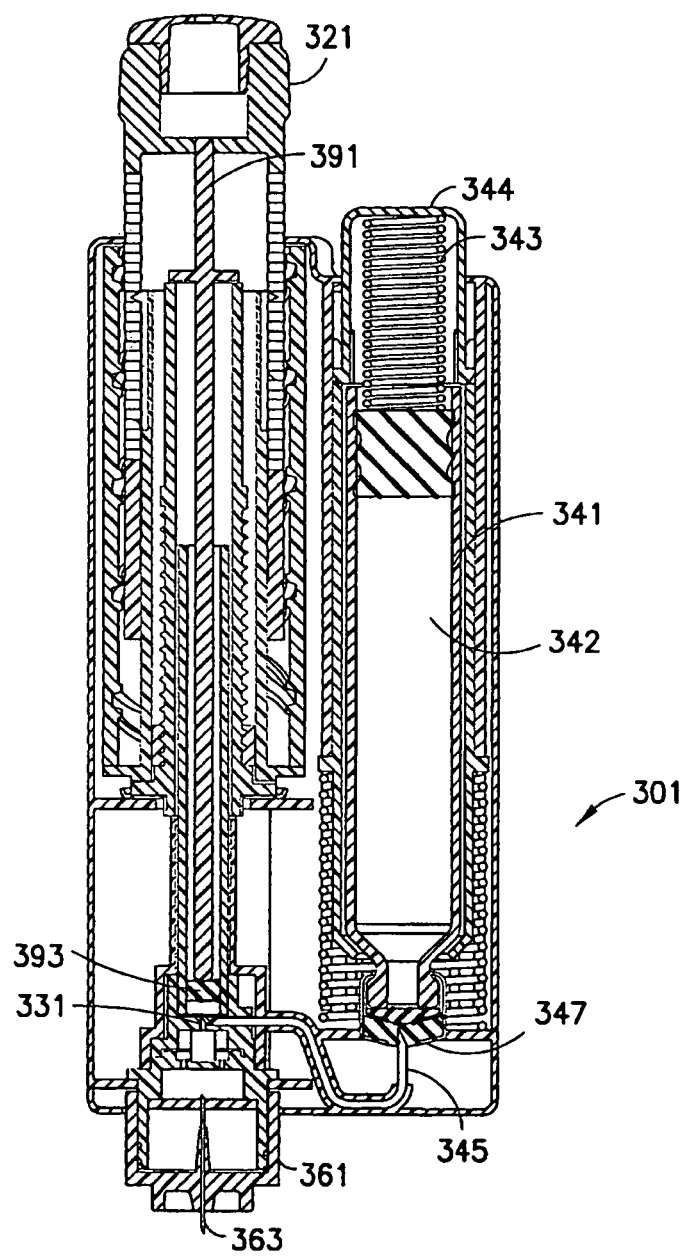
FIGS. 16 and 17 illustrate filling the secondary chamber in the drug delivery device of FIGS. 8A-8D.
Figure 17:
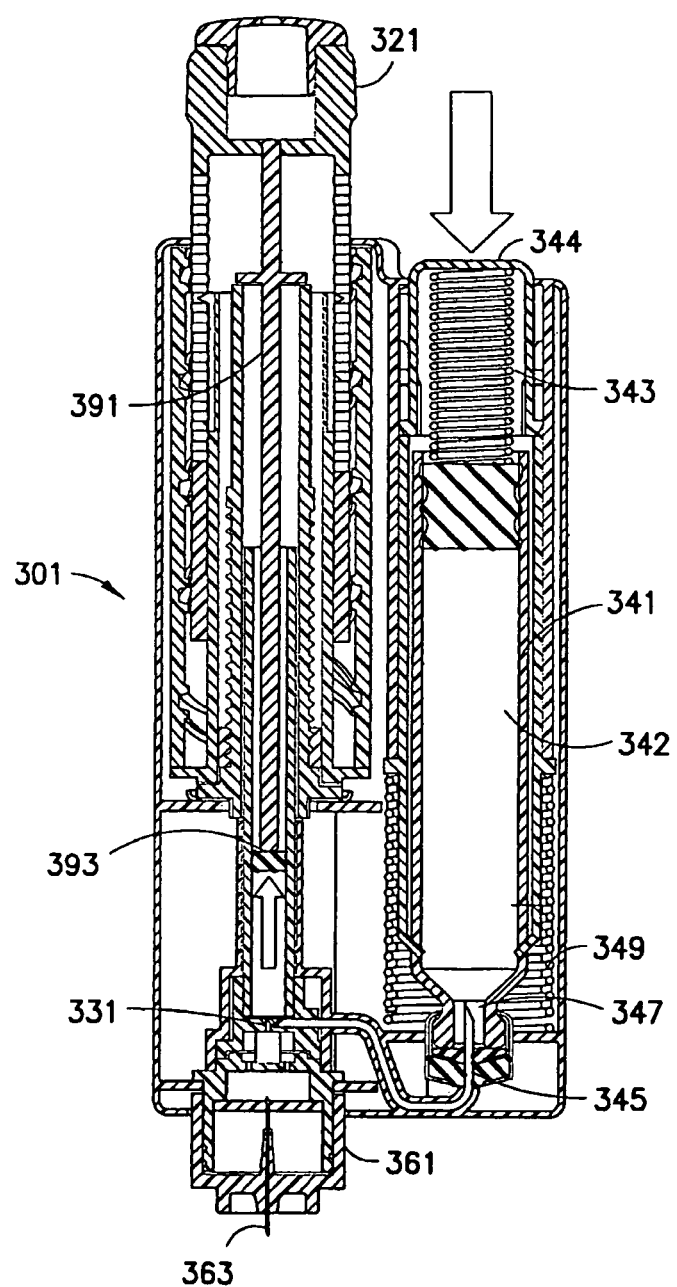

A medicament dose is set and tracked by a stop nut 313 disposed on a track cylinder 317. Preferably, the stop nut 313 is unitarily formed with the track cylinder 317 as one piece. The dose knob 321 threads out of the housing 303 to set the allowable dose in the second chamber 331, as shown in FIGS. 15-17. When the medicament dose is set, the track nut 315 rises with the dose knob 321. The track nut 315 is threadably engaged on an outer surface of the track cylinder 317. A track clutch 319 engages the track nut 315 with the dose knob 321 during the injection (FIGS. 18-21). When the medicament dose is delivered, the track clutch 319 is engaged with the track cylinder 317, such that the track nut 315 maintains its position on the track cylinder 317. The track clutch 319 is engaged with the track cylinder 317 such that the dose knob 321, track cylinder 317, track clutch 319 and track nut 315 rotate together, such that the track nut 315 is not moved by the downward rotation of the dose knob 321. When the medicament dose is being set, as shown in FIG. 19, the clutch spring 320 biases the track clutch 319 away from the track cylinder 317 such that the track clutch 319 rotates with the dose knob 321, thereby rotating the track nut 315 upwardly on the fixed track cylinder 317. Because the track cylinder 317 is disengaged from the track clutch 319, the track cylinder 317 does not rotate with the dose knob 321, track clutch 319 and track nut 315, thereby allowing the track nut 315 to rotate upwardly on the track cylinder 317. Medicament doses can be repeatedly dialed until the track nut 315 has been rotated upwardly on the track cylinder 317 and abuts the stop nut 313, thereby preventing additional medicament doses from being drawn. The position on the stop nut 313 corresponds to a predetermined amount of medicament remaining in the first chamber 342, which is an amount insufficient for an additional medicament dose to be drawn.

Figure 21:
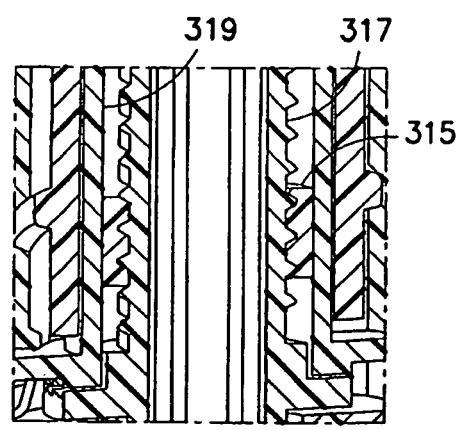

FIGS. 10-15 illustrate the operation of the track nut 315 when the medicament dose is being set. The dose knob 321 is coupled to the track clutch 319 and the track nut 315. When setting the medicament dose, the track nut 315 rotates with the dose knob 321 such that the track nut 315 rises upwardly on the track cylinder 317. A clutch spring 320 of the track clutch 319 keeps the clutch 319 and the track cylinder 317 separated when setting the medicament dose. As shown in FIG. 19, the clutch spring 320 biases the track clutch 319 upwardly away from a base 381 of the track cylinder 317. Grooves on an upper surface of the base 381 of the track cylinder engage grooves on the track clutch 319 when the track clutch 319 engages the track cylinder 317, as shown in FIG. 21.

FIGS. 16 and 17 illustrate the operation of transferring a medicament dose to the second chamber 331. The original drug container (or cartridge) 341 moves upwardly and has the first chamber 342 therein in which the medicament is stored. A spring 343 within the cartridge 341 is always loaded. A needle 345 is embedded in a septum 347. The container 341 is pushed downwardly from a first position (FIG. 16) to a second position (FIG. 17), thereby causing the needle 345 to pierce the septum 347 and transferring the medicament dose to the second chamber 331. A spring 349 returns the cartridge 341 to the first position in which the needle 345 is not piercing the septum 347, as shown in FIG. 16.

Figure 18:
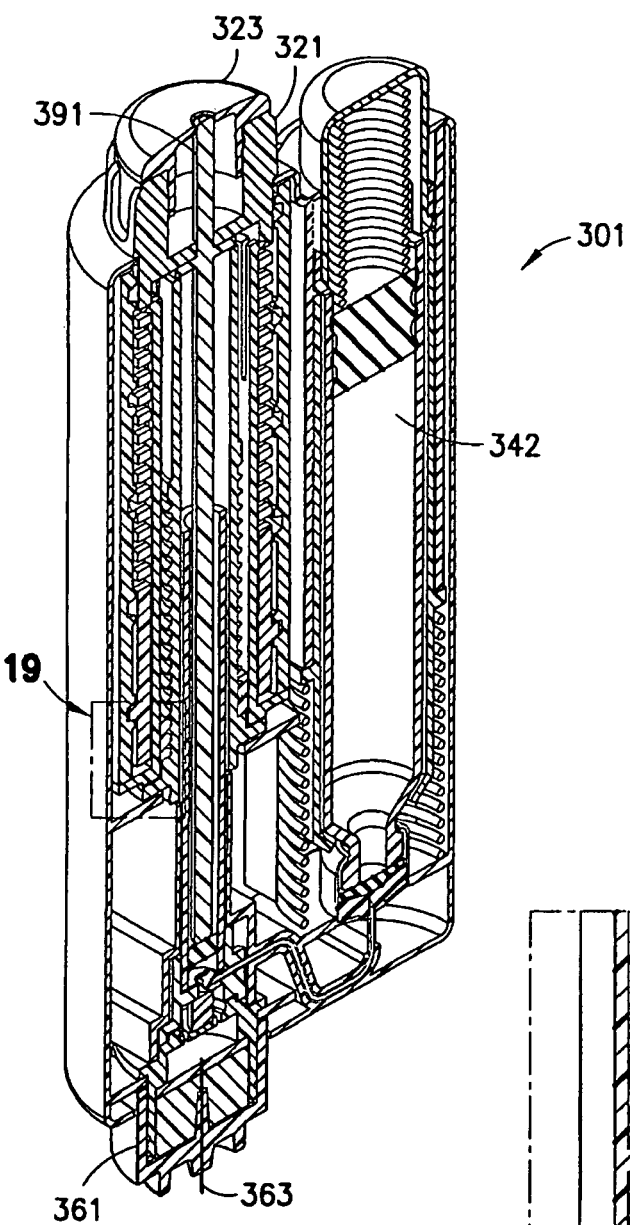
FIGS. 18-21 illustrate delivering the dose with the drug delivery device of FIGS. 8A-8D.
Figure 19:
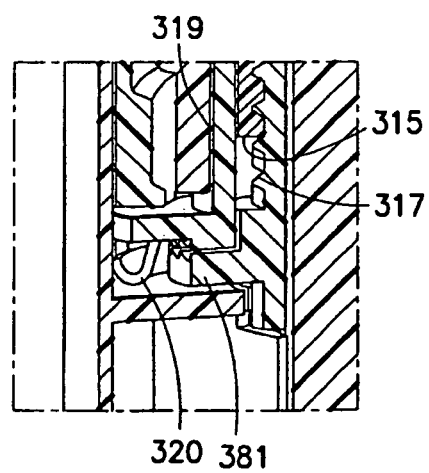
Figure 20:
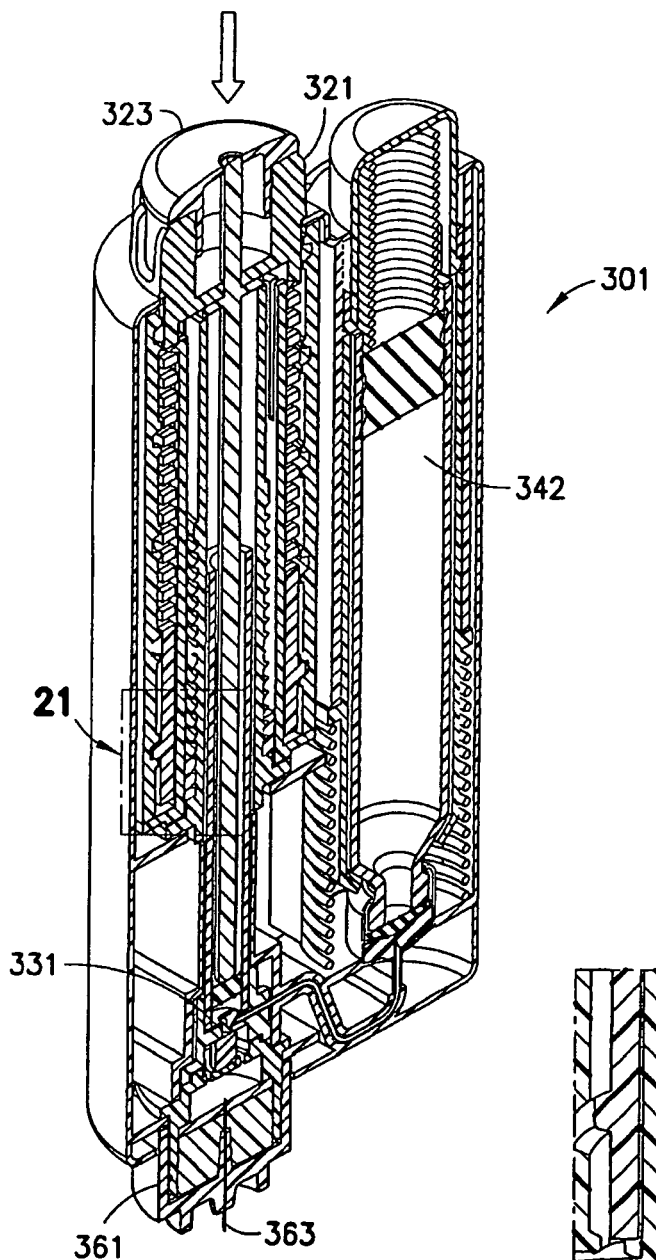

FIGS. 18-21 illustrate delivering the medicament dose with the drug delivery device 301. The spring 320 of the clutch 319 keeps the clutch 319 and the track cylinder 317 separated during the dose setting such that the track nut 315 moves upwardly along the track cylinder as the dose knob 321 is withdrawn to a second position (FIG. 18). The amount the dose knob 321 is withdrawn determines the size of the second chamber, thereby determining the size of the medicament dose. When the dose button 323 is pushed downwardly to a first position (FIG. 9) to deliver the medicament dose (by moving the drive screw 391 and stopper 393 downwardly through the second chamber 331), the clutch 319 engages the track cylinder 317 such that the track cylinder 317, the track nut 315 and the clutch 319 rotate together. Therefore, the track nut 315 does not move away from the stop nut 313 during delivery of the medicament dose. Accordingly, when a medicament dose is next set, the track nut 315 moves upwardly closer to the stop nut 313 on the track cylinder 317. When the track nut 315 abuts the stop nut 313 on the track cylinder 317, the dose knob 321 is prevented from moving such that a further medicament dose is prevented from being drawn from the first chamber 342 to the second chamber 331.

Alternatively, the drug delivery device according to exemplary embodiments of the present invention can be used as a reconstituting drug delivery system. The first chamber contains a diluent. The second chamber, which can be removable/replaceable, contains a solid drug. Accordingly, the drug delivery device enables a reconstitution or resuspension system. The first chamber can store sufficient diluent for many injections, and the second chamber can store a solid drug for fewer injections, such as one or two. Accordingly, the drug delivery device according to exemplary embodiments of the present invention can be used as a reconstitution system, including as a reconstitution system for high pressure injections.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A dual-chambered drug delivery device, comprising:
   a first chamber in which a medicament is stored;
   a spring that compresses said first chamber by applying a spring force;
   a second chamber in fluid communication with said first chamber, a medicament dose being transferred to said second chamber from said first chamber by said spring force prior to injecting said medicament dose, said first chamber being axially movable with respect to said second chamber;
   a needle communicating with said second chamber for injecting said medicament dose into an injection site, a first central longitudinal axis through said needle being parallel to and spaced from a second central longitudinal axis through said first chamber; and
   a dose knob rotating from a first position to a second position to draw the medicament dose.

2. The dual-chambered drug delivery device according to claim 1, wherein said second chamber has a smaller cross sectional area than said first chamber.

3. The dual-chambered drug delivery device according to claim 1, wherein a first valve is disposed between said first chamber and said second chamber.

4. The dual-chambered drug delivery device according to claim 3, wherein a second valve is disposed between said second chamber and said needle.

5. The dual-chambered drug delivery device according to claim 4, wherein
   said first valve is open and said second valve is closed when transferring the medicament dose from the first chamber to the second chamber, and
   said first valve is closed and said second valve is open when injecting the medicament dose from said second chamber through said needle and into the injection site.

6. The dual-chambered drug delivery device according to claim 1, wherein the medicament dose is transferred through a conduit from said first chamber to said second chamber.

7. A dual-chambered drug delivery device, comprising:
   a housing;
   a cartridge disposed in said housing and having a first chamber in which a medicament is stored, said cartridge being axially movable in said housing;
   a spring that compresses said first chamber by applying a spring force;
   a second chamber disposed in said housing and being in fluid communication with said first chamber, a medicament dose being transferred to said second chamber from said first chamber by said spring force prior to injecting said medicament dose;
   a needle communicating with said second chamber for injecting said medicament dose into an injection site, a first central longitudinal axis through said needle being parallel to and spaced from a second central longitudinal axis through said first chamber; and a dose knob rotating out of said housing from a first position to a second position to draw the medicament dose.

8. The dual-chambered drug delivery device according to claim 7, wherein said second chamber has a smaller cross sectional area than said first chamber.

9. The dual-chambered drug delivery device according to claim 7, wherein said cartridge is moved axially from a first position to a second position to transfer the medicament dose from said first chamber to a second chamber; and a second spring returns said cartridge to said first position after the medicament dose is in said second chamber.

10. The dual-chambered drug delivery device according to claim 7, wherein a track nut is rotated on a threaded portion of a track cylinder in response to the rotation of said dose knob.

11. The dual-chambered drug delivery device according to claim 10, wherein said dose knob is rotated to said first position to inject the medicament dose, said track nut not rotating on said track cylinder during the injection.

12. The dual-chambered drug delivery device according to claim 11, wherein a stop nut is disposed on said track cylinder, and when said track nut abuts said stop nut, further medicament doses are prevented from being drawn.

13. The dual-chambered drug delivery device according to claim 12, wherein said stop nut is unitarily formed as one piece with said track cylinder.

14. The dual-chambered drug delivery device according to claim 12, wherein a track clutch is disposed between said dose knob and said track cylinder, said track clutch being disengaged from said track cylinder during the dose setting to allow said track nut to rotate on said track cylinder, and said track clutch being engaged with said track cylinder during the injection to prevent said track nut from rotating on said track cylinder.

15. The dual-chambered drug delivery device according to claim 14, wherein a clutch spring biases the track clutch away from the track cylinder.

16. The dual-chambered drug delivery device according to claim 7, wherein said first central longitudinal axis through said needle is parallel to and spaced from a second central longitudinal axis through said cartridge.

17. A method of injecting medicament using a dual-chambered drug delivery device, comprising the steps of:

storing a medicament in a first chamber;

rotating a dose knob from a first position to a second position to draw a medicament dose;

transferring the medicament dose by a spring force from the first chamber to a second chamber by axially moving the first chamber from a first position to a second position with respect to the second chamber; and injecting the medicament dose from the second chamber into an injection site by a needle, wherein a first central longitudinal axis through the needle is parallel to and spaced from a second central longitudinal axis through the first chamber.

18. The method of injecting medicament using a dual-chambered drug delivery device according to claim 17, further comprising tracking the amount of the medicament stored in the first chamber.

19. The method of injecting medicament using a dual-chambered drug delivery device according to claim 18, further comprising preventing the medicament dose from being transferred when the stored medicament being tracked is less than a predetermined amount.

* * * * *